United States Patent [19]

Hayashi

[11] Patent Number: 5,202,417
[45] Date of Patent: Apr. 13, 1993

[54] 60-AMINO-ACID POLYPEPTIDE
[75] Inventor: Kyozo Hayashi, Gifu, Japan
[73] Assignee: Takeda Chemical Industries, Ltd., Osaka, Japan
[21] Appl. No.: 396,937
[22] Filed: Aug. 21, 1989
[30] Foreign Application Priority Data Feb. 16, 1989 [JP] Japan .................................. 1-35111
[51] Int. Cl.$^5$ ..................... A61K 37/00; A61K 37/02; C07K 5/00; C07K 7/00
[52] U.S. Cl. ................................... 530/324; 530/300; 514/12
[58] Field of Search ............... 530/300, 324; 435/69.1, 435/240.2; 514/12

[56] References Cited

PUBLICATIONS

Rio et al, Biological Abstracts, (1988), BA86:82222.
Mori et al, Biological Abstracts (1987), BA84:68106.
Naito et al., Biological Abstracts (1983), BA76:50786.
Luqmani et al, Biological Abstracts (1989) BA89:50020.
Mori et al., Biochemical and Biophysical Research Communications, vol. 155, No. 1, 366–372 (1988).

*Primary Examiner*—Merrell C. Cashion, Jr.
*Assistant Examiner*—A. M. Davenport
*Attorney, Agent, or Firm*—David G. Conlin; Ernest V. Linek

[57] ABSTRACT

Disclosed is a novel polypeptide whose N-terminus is EAQ and which is composed of 60 amino acids. The polypeptide is produced from human breast cancer cell MCF7, or human gastric cancer cell MKN-45 or KATO-III, which polypeptide has a isoelectric point of 4.3, a molecular weight of 6,661 and the following amino acid sequence:

EAQTETCTVAPRERQNCGFPGVTPSQCANK

GCCFDDTVRGVPWCFYPNTIDVPPEEECEF.

1 Claim, 4 Drawing Sheets signal peptidase (peptide obtained by the present inventor)

```
    1           11          21 ↓        31          41          51          61          71
    MATMENKVICALVLVSMLALGTLAEAQTETCTVAPRERQNCGFPGVTPSQCANKGCCFDDTVRGVPWCFYPNTIDVP
                              ↑         ↑
                    Enzyme-cleaved sites predicted by Chambon et al.

81
    PEEECEF
```

FIG. 5

60-AMINO-ACID POLYPEPTIDE

BACKGROUND OF THE INVENTION

The present invention relates to a novel polypeptide produced by certain kinds of cancer cells, more particularly to a polypeptide whose N-terminus is EAQ and which is composed of 60 amino acids.

It has been reported that 'transformed cells' react with substances produced by themselves and thereby self-propagate [M. B. Spora et al., Nature 313, 745–747 (1985)]. This mechanism is called autocrine and has received much attention in connection with carcinomas and the like in recent years.

Of the cancer cells which are 'transformed cells', human breast cancer cell MCF7, for example, has been shown to secrete transforming growth factors α, β and γ [Dickson et al., Cancer Res. 46, 1707–1713 (1986)], insulin-like growth factor [Haff et al., Cancer Res. 46, 4613–4619 (1986)]and platelet-derived growth factor [Brouzert et al., Pro. Natl. Acad. Sci. U.S.A. 84, 5763–5767 (1987)].

As to mRNA induced with estrogen in human breast cancer cells, its complete nucleotide sequence has been elucidated by Chambon et al., and the presence of a polypeptide (9140 daltons) composed of 84 amino acids has been predicted from this nucleotide sequence. It is further predicted from this amino acid sequence that a polypeptide actually secreted may be one (6450 daltons) composed of 58 amino acids or one (6970 daltons) composed of 63 amino acids [Chambon et al., Nucleic Acids Research 12, No. 6, 2861–2878 (1984), and Chambon et al., DNA 4, 11–21 (1985)]. However, this is nothing more than an assumption, and such secreted polypeptides have not been actually isolated and purified to such a degree that their amino acid sequence can be determined.

Thus there has been a long felt need in this field for the isolation and purification of the polypeptides secreted by the breast cancer cells MCF7 and the like, particularly for the elucidation of any relationship between the

SUMMARY OF THE INVENTION

In order to examine the relationship between the MCF7 cells thus secreting various growth factors and epidermal growth factor (hereinafter referred to as EGF) which is a kind of growth factor, we established an enzyme immuno assay (hereinafter referred to as EIA) which can assay human EGF, and tried to determine it in the culture solutions of MCF7 and human gastric cancer cells MKN-45 and KATO-III. As a result, it was discovered that a novel substance which was immunoreactive to the EIA but different from EGF was produced in the culture. It is conceivable that this substance was detected because another antibody was present in the enzyme immuno assay in addition to an antibody against EGF.

In order to obtain more information about the relationship between this novel immunoreactive polypeptide and carcinoma, we purified this polypeptide and determined its structure.

The present invention provides a novel peptide whose N-terminus is EAQ and which is composed of 60 amino acids. This polypeptide is produced by human breast cancer cell MCF-7 or human gastric cancer cells MKN-45 or KATO-III. Further, this immunoreactive polypeptide has a isoelectric point of 4.3, a molecular weight of 6,661 daltons and the following amino acid sequence:

EAQTETCTVAPRERQNCGFPGVTPSQCANK

GCCFDDTVRGVPWCFYPNTIDVPPEEECEF.

BRIEF DESCRIPTION OF THE DRAWINGS

FIG. 5 is the amino acid sequence of a precursor of the polypeptide according to the present invention, wherein a position where a signal peptidase acts to provide the mature polypeptide is shown in comparison to the enzyme-cleaved sites predicted by Chambon et al.

DESCRIPTION OF THE PREFERRED EMBODIMENT

Figure 1:
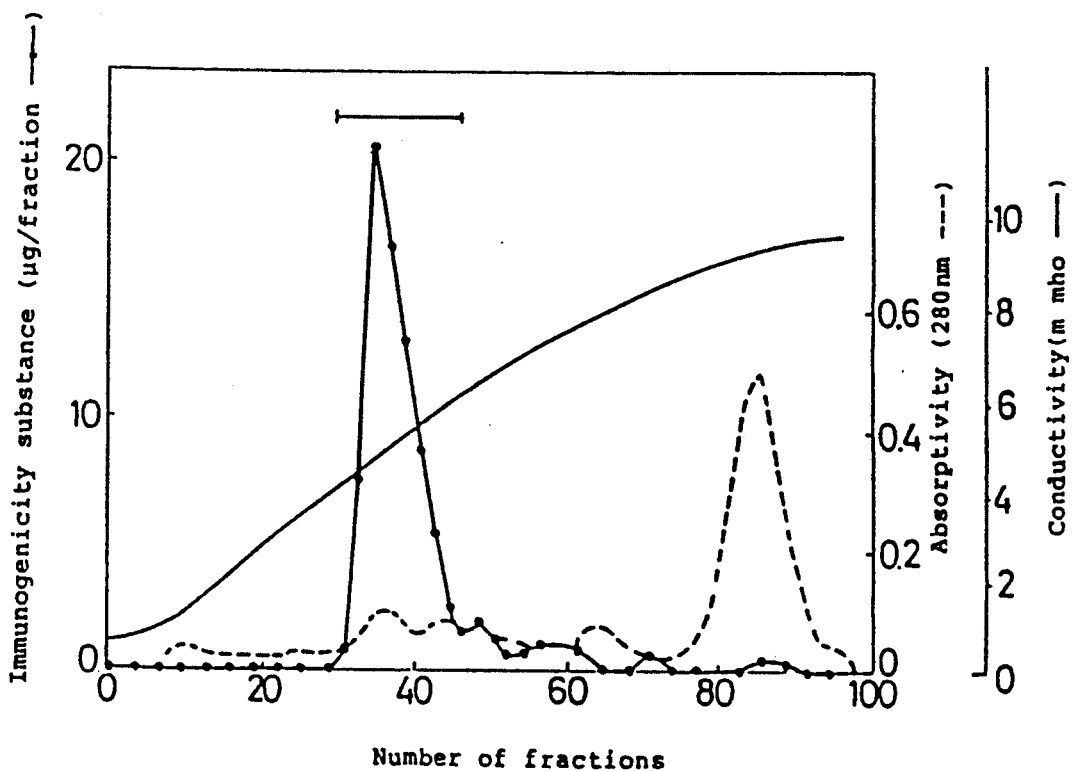
FIGS. 1 to 3 are graphs showing results obtained by purifying a polypeptide of the present invention, by anion exchange chromatography, gel permeation chromatography and reverse-phase high performance liquid chromatography, respectively.

The polypeptide of the present invention is produced by cultivating the cells MCF-7, or MKN-45 or KATO-III. The cultivation of these cancer cells is conducted by methods known in the art. Serum cultures using a serum containing medium or serum-free cultures may be used for the cultivation. However, for the purpose of isolating the polypeptide of the present invention, the serum-free cultures are highly preferable. Of many suitable cultivating procedures known in the art, monolayer subculturing is preferably employed. As media for the cultivation, the media usually used for the cultivation of higher animal cells such as Dulbecco's modified Eagle's minimal essential medium (DMEM) and Ham F-10 medium are preferable. The media are used in amounts of 0.05 to 5 ml, preferably 0.1 to 0.2 ml for $10^5$ cancer cells. The cultivation term is preferably 2 to 10 days, and in the case of serum-free cultures 2 to 3 days is most preferable, in the case of serum cultures 3 to 4 days is most preferable. The cultivation temperature is usually $37° \pm 1°$ C.

For the isolation and the purification of the polypeptide of the present invention, there may be used known isolating and purifying methods for polypeptides, such as extraction, ion exchange or gel permeation chromatography, high performance liquid chromatography, electrophoresis and recrystallization. For the purpose of the present invention, ion exchange or reverse-phase chromatography or high performance liquid chromatography is particularly suitable.

It has become clear that the polypeptide thus purified is composed of 60 amino acids and is a part of the PS2 precursor protein determined by Chambon et al., and composed of 84 amino acids which is coded for with cDNA of PS2 polypeptide probably secreted from the human breast cancer cells [DNA 4, 11–21 (1985)]. As described above, however, Chambon et al. have merely anticipated amino acids from cDNA, and such isolation and purification of the polypeptide as those in the present invention have not been carried out. The novel polypeptide according to the present invention is immunoreactive to anti-PS2 antibodies.

Chambon et al. have further predicted that an enzyme acts at the 22- or the 27-position of this precursor to provide the mature polypeptide composed of 58 or 63 amino acids. However, the polypeptide actually obtained in the present invention is produced by the action of the enzyme at the 25-position and composed of 60 amino acids. This polypeptide is three lower or two higher than the polypeptide predicted by Chambon et al. in number of amino acids, and is a novel polypeptide first isolated and purified in the present invention.

An assay system used for detecting the polypeptide of the present invention was prepared in the following manner.

Plate Sensitization

200 μg/ml of an IgG fraction (purified from rabbit serum) containing anti-hEGF antibody was added to 50 mM of Tris-HCl (pH 8.0), and the mixture was poured to a microplate having 96 wells (Sumitomo Bakelite Co.) in an amount of 100 μl/well. After the reaction was conducted at 37° C. for 3 hours, the solution was discarded. Buffer A was further added thereto and blocking was carried out. Then, the resultant product was further allowed to stand at 4° C. overnight. The composition of the buffer A is as follows:
0.1 M phosphate buffer (pH 7.0)
0.1 % bovine serum albumin (BSA)
0.3 M NaCl
0.1 % NaN$_3$
1 mM MgCl$_2$ Using this assay system, an assay was performed in the following manner.

Assay

A plate was washed once with 200 μl/well of buffer A just prior to the use thereof. Then, 100 μl/well of buffer A and 100 μl of a sample were added to the plate in duplicate, and reacted with each other at 4° C. overnight, followed by washing with four 200 μl/well portions of a washing buffer. 100 μl/well of Fab'-HRP conjugate (which was prepared by diluting 1000 times a liquid concentrate with the washing buffer) was added thereto, and reacted at 37° C. for 4 hours. Then, the reaction product was washed with four 200 μl/well portions of the washing buffer, and 100 μl/well of 0.6 % HPPA[3-(p-hydroxyphenyl)propionic acid]solution in 0.1 M phosphate buffer (pH 7.0) and 100 μl/well of 0.015 % H$_2$O$_2$ were added thereto. Then, the reaction was conducted at 37° C. for more than 1 hour, and terminated with 50 μl/well of 0.1 M glycine-NaOH (pH 10.3). The resultant product was transferred to a Dynamic TM microfluor (for fluorescent enhancer), and the fluorescence was measured with an immunoreader (365 nm excitation, 415 nm fluorescence measurement). The following were used as controls.
Negative: H$_2$O (0)
Positive: 1.0 μg/ml of kinin in 0.1 N sulfuric acid (100)

The polypeptide of the present invention is produced and secreted from certain kinds of cancer cells, and is anticipated to be related to carcinoma. For example, measuring the concentration or distribution of the polypeptide in cells or tissues, makes possible the diagnosis of cancers or the understanding of the state of cancer development. Hence, this polypeptide can be useful for the elucidation of the growth mechanism of cancer cells and in its turn the determination of the efficacy of therapeutic agents for carcinoma. This polypeptide has high homology with the known pancreatic spasmolytic enzyme (PSP) [Jorgensen et al., *Regulatory Peptide* 3, 207–219 (1982)]secreted from the pancreas, and can be assumed to have intestinal motility depression activity which the above enzyme has and further muscular contraction relaxation activity. According to the present invention, the polypeptide can be produced and purified in large amounts by genetic engineering techniques.

In the present specification and the accompanying drawings, the abbreviations of amino acids and the like are based on those adopted by IUPAC-IUB Commission on Biochemical Nomenclature or those customarily used in the art. Examples of the abbreviations are as follows:
G: Glycine
A: Alanine
V: Valine
L: Leucine
I: Isoleucine
S: Serine
T: Threonine
C: Cysteine
M: Methionine
E: Glutamic acid
D: Aspartic acid
K: Lysine
R: Arginine
H: Histidine
F: Phenylalanine
Y: Tyrosine
W: Tryptophan
P: Proline
N: Asparagine
Q: Glutamine When the optical isomers are capable of existing with respect to the amino acids, the L-forms are represented unless otherwise specified.

The present invention will hereinafter be described with the following Example and the accompanying drawings. It is understood of course that these do not intend to limit the scope of the invention.

EXAMPLE

1. Purification of Novel Protein (a) Cultivation of MCF-7 Cells

Using a plastic flask (175 cm$^2$) supplied by Nunc, MCF-7 cells were cultivated at 37° C. in an atmosphere of 5% CO$_2$/95% air in Dulbecco's modified Eagle's minimal essential medium (DMEM) containing 10% bovine serum, insulin (12×10$^{-6}$ M), β-estradiol (10$^{-8}$ M), glutamine (0.3 mg/ml), penicillin (50 units/ml) and streptomycin (0.05 mg/ml). After the sufficient propagation of the cells, the cells were washed with a phosphate buffer, and the medium was replaced with a serum-free medium prepared by mixing DMEM and HAM F12 in a ratio of 1 : 1. The medium contains β-estradiol (10$^{-8}$ M) After cultivation for 24 to 48 hours, the medium was collected and centrifuged at 5,000 rpm for 30 minutes.

(b) Anion-Exchange Chromatography by using DEAE-Sephadex A-25

The sample obtained in (a) was dialyzed against 0.05 M ammonium acetate buffer (pH 5.5), using a dialysis membrane (Spectrapor 3), and then allowed to flow at a flow rate of 50 ml/hour in a Sephadex A-25 column (1.7 cm in inside diameter and 43.5 cm in length) previously equilibrated with the same buffer. The column was washed with the same buffer, and a linear gradient solution of 500 ml of 0.05 M ammonium sulfate buffer (pH 5.5) and 500 ml of 2 M ammonium acetate buffer (pH 5.5) was used for elution. Positive fractions in an enzyme immuno assay (EIA) were collected and lyophilized. The results are shown in FIG. 1.

(c) Gel Permeation

Figure 2:
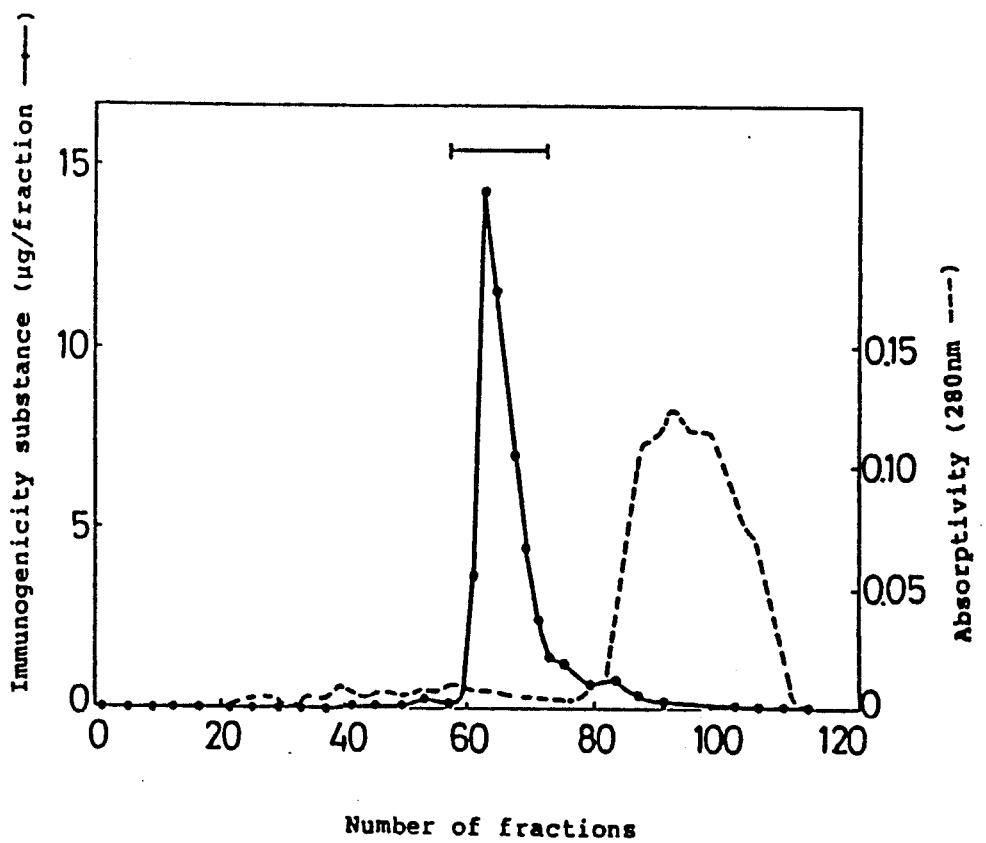

The lyophilized and dried powder obtained in (b) was dissolved again in 10 ml of 1% acetic acid, and allowed to flow at a flow rate of 12 ml/hour in a Sephadex G-50 superfine column (2.5 cm in inside diameter and 100 cm in length) equilibrated with 1% acetic acid. After elution with the same 1% acetic acid, positive EIA fractions were collected and dried under reduced pressure. The results are shown in FIG. 2.

(d) Reverse-Phase High Performance Liquid Chromatography

Figure 3:
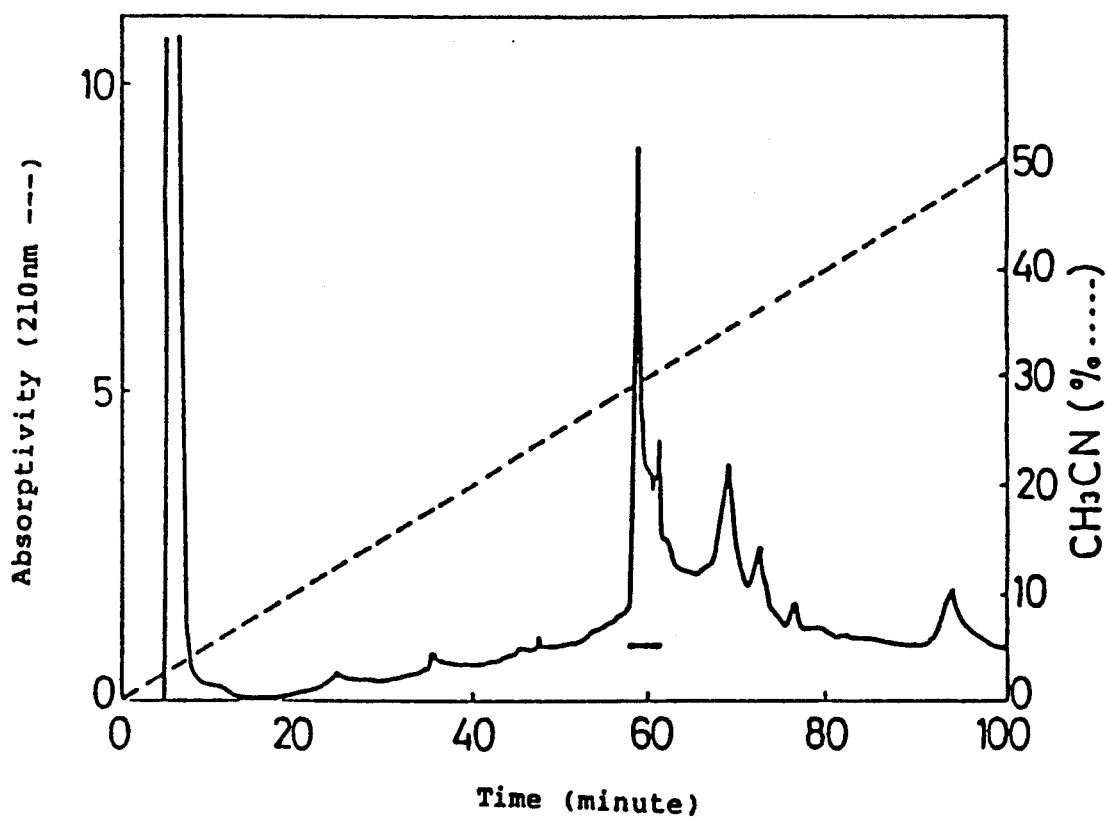

The dried product obtained under reduced pressure in (c) was dissolved in 100 ml of 10% trifluoroacetic acid, o and allowed to flow in a μBondapak C18 column at a flow rate of 0.7 ml/minute. Elution from the column was conducted with a linear gradient acetonitrile from 0% to 50 containing 0.1% TFA for 100 minutes. The detection of the protein from the column was carried out at 210 nm. The results are shown in FIG. 3.

(e) Determination of Amino Acid Sequence

Figure 4:
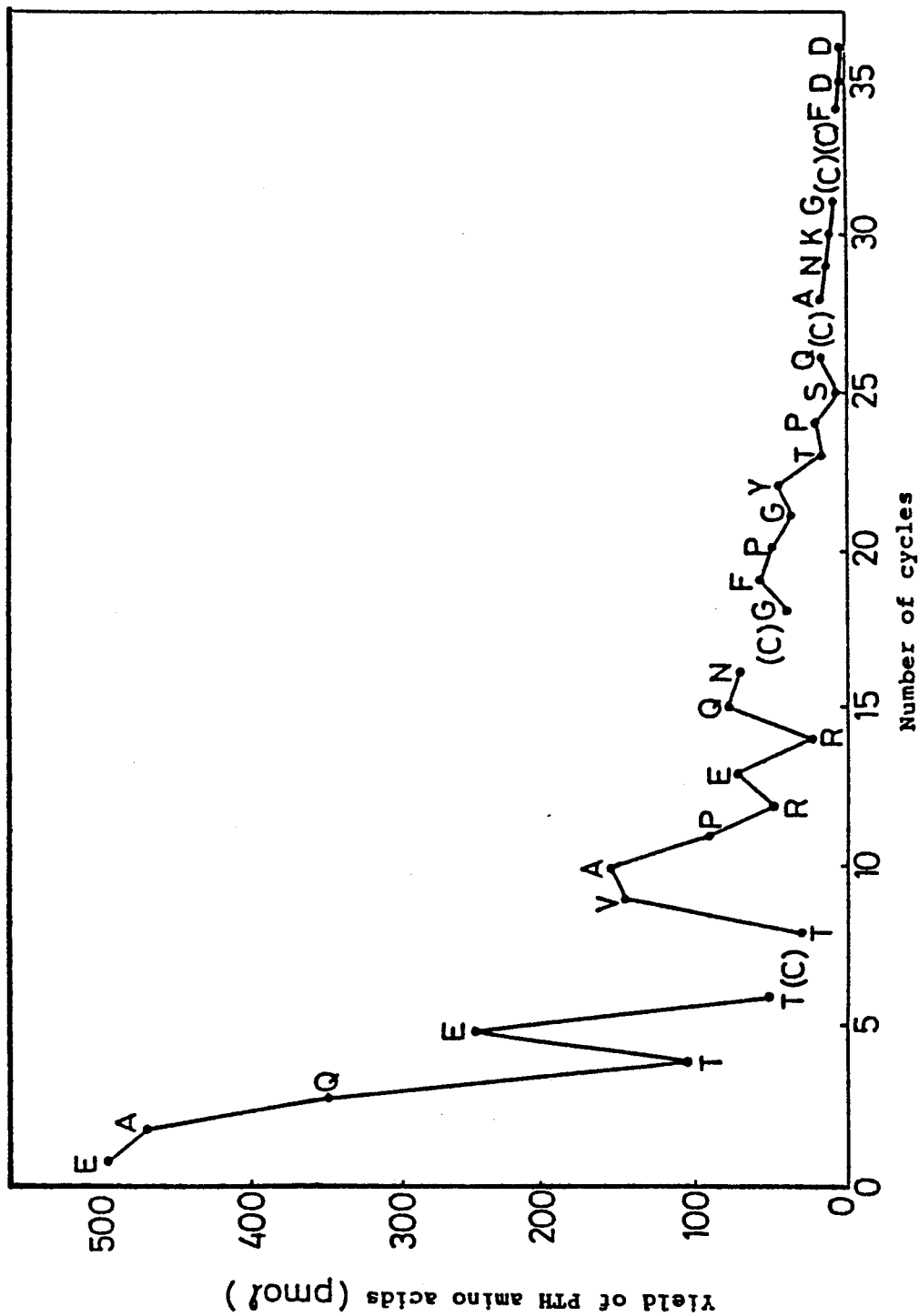
FIG. 4 is a graph showing the determination of the amino acid sequence of the polypeptide according to the present invention.

The amino acid sequence of the purified polypeptide was automatically determined by means of an automatic amino acid sequencer, Model-129A (Applied Biosystems). The sequence of PTH amino acids obtained by Edman degradation was as follows, when shown from the N-terminus (see FIG. 4.):

EAQTETCTVAPRERQNCGFPGVTPSQ-CANKGCCFDD

Further, portions subsequent and preceding to the above-mentioned amino acids, which portions are anticipated from a gene (DNA), are shown together with the above-mentioned amino acids as follows:

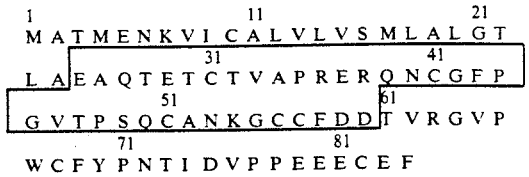

The box shows the sequence determined previously.

(f) The recovery rate of this polypeptide upon purification is 21.8%. It has become clear that the purified polypeptide is composed of 60 amino acids and is a part of the PS2 precursor protein determined by Chambon et al. and composed of 84 amino acids which is coded for with cDNA of the PS2 polypeptide. However, Chambon et al. have not actually purified the protein to such a degree that their amino acid sequence can be analyzed as with the present invention, and have merely indicated the amino acid sequence anticipated from cDNA.

Chambon et al. have further assumed that an enzyme acts at the 22- or the 27-position of this precursor to provide the mature polypeptide composed of 58 or 63 amino scids. However, the polypeptide obtained in the present invention is produced by the action of the signal peptidase at the 25-position and composed of 60 amino acids. This polypeptide is three lower or two higher than the polypeptide predicted by Chambon et al. in the number of amino acids. Also in this sense, the polypeptide of the present invention can be said to be novel (see FIG. 5).

The following references, which are referred to for their disclosures at various points in this application, are incorporated herein by reference.

Nature 313, 745-747 (1985)
Cancer Res. 46, 1707-1713 (1986)
Cancer Res. 46, 4613-4619 (1986)
Pro. Natl. Acad. Sci. U.S.A. 84, 5763-5767 (1987)
Nucleic Acids Research 12, No. 6, 2861-2878 (1984)
DNA 4, 11-21 (1985)
Regulatory Peptide 3, 207-219 (1982)

What is claimed is:

1. The claim A polypeptide consisting of the amino acid sequence:

EAQTETCTVAPRERQNCGFPGVTPSQCANK

GCCFDDTVRGVPWCFYPNTIDVPPEEECEF.

* * * * *

UNITED STATES PATENT AND TRADEMARK OFFICE
CERTIFICATE OF CORRECTION

PATENT NO. : 5,202,417
DATED : April 13, 1993
INVENTOR(S) : Hayashi

It is certified that error appears in the above-identified patent and that said Letters Patent is hereby corrected as shown below:

Column 6, line 44, delete "The claim".

Signed and Sealed this

Fourth Day of January, 1994

Attest:

BRUCE LEHMAN

Attesting Officer

Commissioner of Patents and Trademarks